United States Patent
Tannoury et al.

(10) Patent No.: US 11,612,544 B2
(45) Date of Patent: Mar. 28, 2023

(54) INTRAVENOUS FLUID ADMINISTRATION CATHETER ASSEMBLY

(71) Applicant: BENTA PHARMA INDUSTRIES EUROPE SARL, Paris (FR)

(72) Inventors: Bernard Tannoury, Dbayyeh (LB); Daniel Boulos, Jounieh (LB)

(73) Assignee: MEDWORKS SARL, Saint-Genis-Laval (FR)

(*) Notice: Subject to any disclaimer, the term of this patent is extended or adjusted under 35 U.S.C. 154(b) by 140 days.

(21) Appl. No.: 16/384,115

(22) Filed: Apr. 15, 2019

(65) Prior Publication Data
US 2019/0343724 A1 Nov. 14, 2019

(30) Foreign Application Priority Data
May 9, 2018 (EP) .................................. 18171510

(51) Int. Cl.
*A61J 1/20* (2006.01)
*A61M 5/162* (2006.01)
(Continued)

(52) U.S. Cl.
CPC .............. *A61J 1/2058* (2015.05); *A61J 1/201* (2015.05); *A61M 5/162* (2013.01);
(Continued)

(58) Field of Classification Search
CPC ........ A61J 1/2058; A61J 1/201; A61M 5/162; A61M 25/0097; A61M 39/26;
(Continued)

(56) References Cited

U.S. PATENT DOCUMENTS

| 4,191,183 A | 3/1980 | Mendelson |
| 5,078,699 A * | 1/1992 | Haber ................. A61M 5/1408 604/250 |

(Continued)

FOREIGN PATENT DOCUMENTS

| DE | 20 2016 100371 U1 | 6/2017 |
| DE | 20 2017 107087 U1 | 3/2018 |

(Continued)

OTHER PUBLICATIONS

English Translation of DE-202016100371-U1 (Year: 2016).*
(Continued)

*Primary Examiner* — Susan S Su
*Assistant Examiner* — Eric Rassavong
(74) *Attorney, Agent, or Firm* — Ladas & Parry LLP

(57) ABSTRACT

The assembly comprises: a stand for hanging a container of a main liquid, a spike, to be introduced into the container of main liquid, a multi-inlet connector with inlet tubings, to be connected to containers of additional liquids and to the container of main liquid through the spike, and an outlet tubing to be connected to a luer syringe to be introduced into a patient. The length of the spike inlet tubing of the connector has a length determined for, during use of the assembly with a container of main liquid, keeping the connector hung up on the stand through the spike and the container of main liquid. Thanks to the invention, the problem of the tubing traffic is solved.

2 Claims, 2 Drawing Sheets

Figure 3:
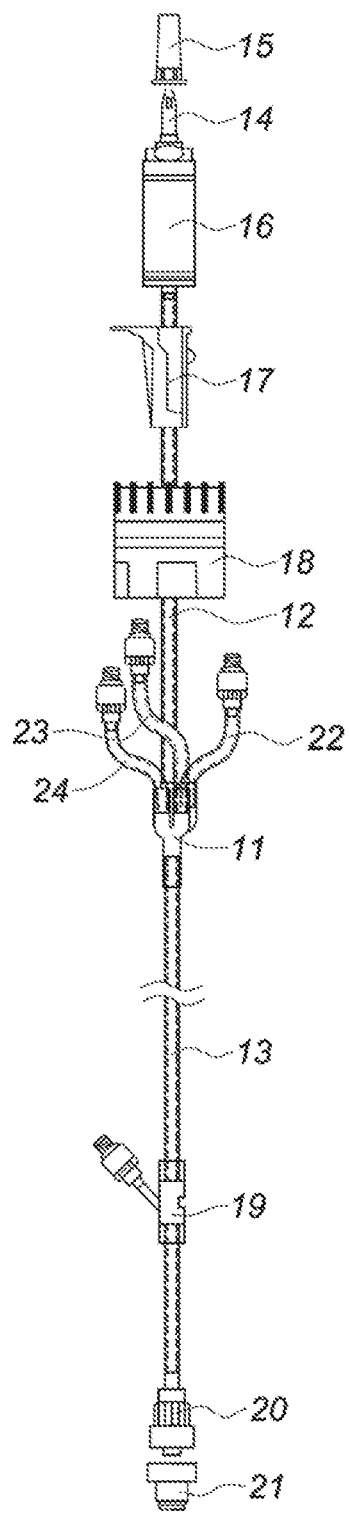

(51) Int. Cl.
*A61M 39/26* (2006.01)
*A61M 25/00* (2006.01)
*A61M 39/08* (2006.01)

(52) U.S. Cl.
CPC ........ *A61M 25/0097* (2013.01); *A61M 39/26* (2013.01); *A61M 2039/082* (2013.01)

(58) Field of Classification Search
CPC ...... A61M 2039/08; A61M 2039/1083; A61M 5/1408; A61M 2039/082
See application file for complete search history.

(56) References Cited

U.S. PATENT DOCUMENTS

| | | | |
|---|---|---|---|
| 2006/0089604 A1 | 4/2006 | Guerrero | |
| 2009/0306621 A1* | 12/2009 | Thome, Jr. | A61M 39/223 604/82 |
| 2012/0203205 A1* | 8/2012 | Briggs | A61M 5/1407 604/519 |
| 2012/0330246 A1* | 12/2012 | Browne | A61M 5/1407 604/244 |
| 2017/0205834 A1* | 7/2017 | Ambrosina | A61M 5/14224 |

FOREIGN PATENT DOCUMENTS

| | | | |
|---|---|---|---|
| WO | 2004/045704 A2 | 6/2004 | |
| WO | 2004045704 A3 | 6/2004 | |
| WO | WO-2004045704 A2 * | 6/2004 | ............ A61M 39/10 |

OTHER PUBLICATIONS

Definition of "Fixed." from Merriam-Webster.com Thesaurus, Merriam-Webster, https://www.merriamwebster.com/dictionary/fixedly. Accessed Jan. 7, 2022. (Year: 2022).*
European Search Report for counterpart Application No. 18171510.3-1122.

* cited by examiner

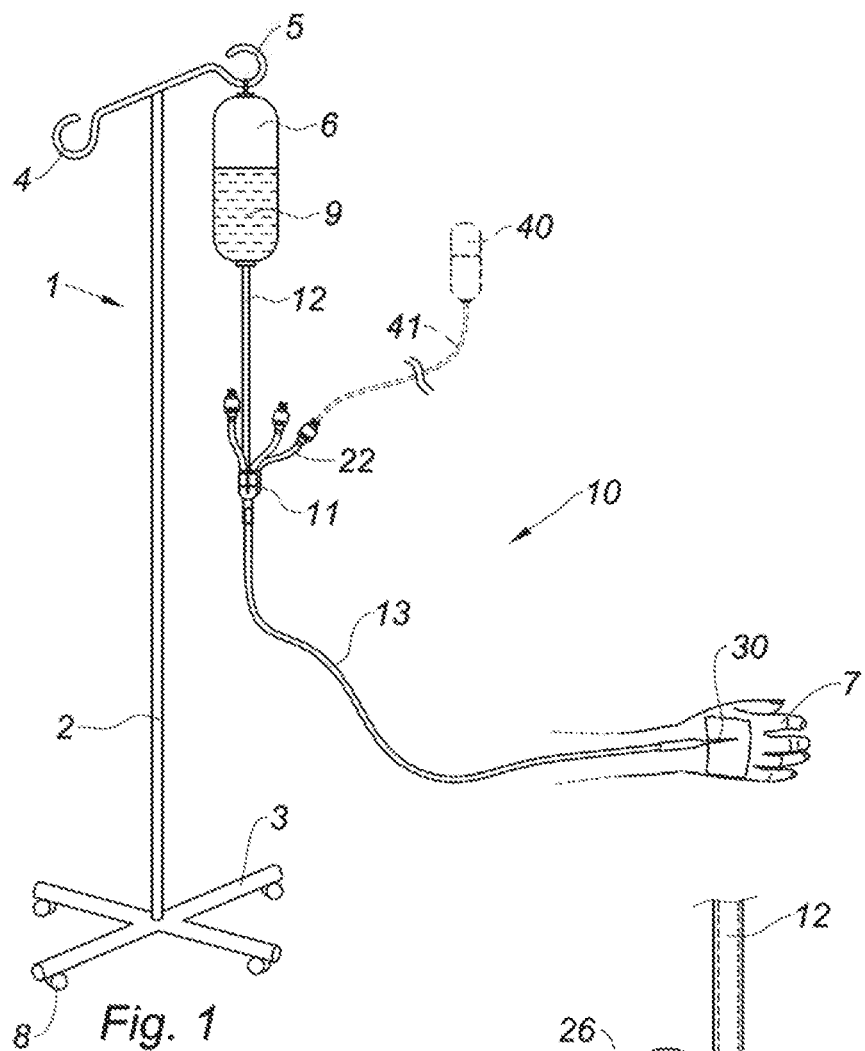
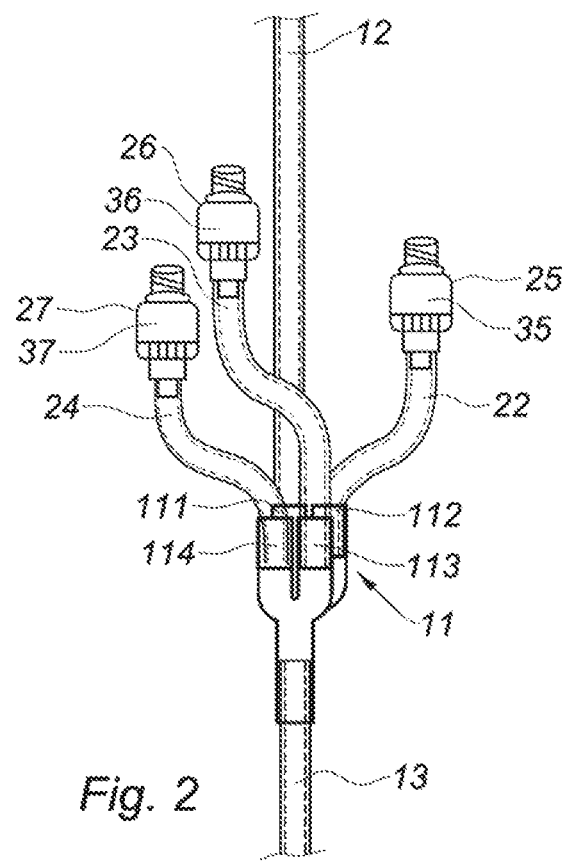

INTRAVENOUS FLUID ADMINISTRATION CATHETER ASSEMBLY

The invention relates to intravenous fluid administration systems. More particularly, it relates to systems arranged for dispensing a main fluid, often serum, along with additional fluids, nutrient and medical fluids.

An intravenous line is inserted into a blood vessel by means of a needle. Once the line, or the catheter, is in place, the needle is removed.

An intravenous fluid administration catheter assembly comprises a spike, to be introduced into a bag or bottle of a main fluid, a drip chamber, a roller clamp, to generate drops, and a flow regulator, to adjust the flow of the drops, a male luer lock and a female luer syringe, with a female luer lock, to be introduced into the patent and tubings in between.

When a second bottle of additional liquid has to be connected to the syringe, a similar set of equipment is used, both sets being connected to an actuator receiving the two liquids for dispensing, at its output, a mixture, through a common tubing, to the syringe.

Other liquids may be dispensed, through other actuators connected in series to the first one.

Another way for dispensing several liquids would be to use a manifold with as many inputs in a tubing, where the serum should flow, as liquids to dispense.

Three problems are at the origin of the invention of the instant case.
1. While considering an intravenous catheter assembly with an actuator having two input tubings, for a main and an additional liquids, and one short output tubing for the mixture, prior to being in operation, the output tubing is closed by a cap. Inside the short output tubing of the actuator, there is air between the actuator and the cap and this is a source of infection. As many actuators, as many sources of infection.
2. While considering an intravenous catheter assembly with a series of tubings, all these tubings arrive onto the body of the patient and they intermingle. It is a mess.
3. An actuator, with two input tubings, includes a two way cock, to be actuated for allowing flow of just one of the two liquids, of both or none of them. Actuation of the cock may affect the good order of the actuator.

The invention of the instant application aims to obviate at least part of these drawbacks.

To this end, the invention relates to
an intravenous fluid administration catheter assembly comprising
   a stand with a hook for hanging a container of a main liquid,
   a spike to be introduced into the container of main liquid,
   a multi-inlet connector with inlet tubings, to be connected to containers of additional liquids and to the container of main liquid through the spike, and an outlet tubing to be connected to a luer syringe to be introduced into a patient,
characterized in that
   the length of the spike inlet tubing of the connector has a length determined for, during use of the assembly with a container of main liquid, keeping the connector hung up on the hook of the stand through the spike and the container of main liquid.

It should be right away clearly pointed out that the hanging situation of the connector in use, thanks to gravity, is not the result of the invention, but its functional means. The connector hanging on the stand, due to its weight, it remains close to the vertical column of the stand, this avoiding the mess of tubings of the prior art, just one single tubing extending away from the stand. And this is the result achieved by the assembly of the instant case, i.e. solving the problem of the tubing traffic.

Preferably, the free end of the additional liquid inlet tubings is closed by a non-return valve advantageously provided within a needleless connector. The valve is normally in a closed state and gets open when the additional liquid inlet tube is connected to a container.

Thus, when the main liquid flows from its container to the luer syringe, through the outlet tubing, the additional liquid inlet tubings, the air having been bailed out of them first, are filled up with the main liquid, so that, when a container of additional liquid is connected to its associated inlet tubing, through its connector and valve, there is no air coming in. The infection issue is thus solved.

The assembly of the instant case, with respect to air, is a closed system. From the spike to the patient, no air can come into the assembly.

Moreover, of great interest also is the fact that the assembly does not include any cock to be actuated.

It should be here mentioned that U.S. Pat. No. 4,512,764 relates to an assembly with a manifold and cocks. CA 2 634 128 relates to an assembly with a connector (junction housing), downstream of the luer connector provided at the end of the central tubing.

The invention shall be better understood upon reading the following description, with reference to the attached drawing, wherein FIG. 1 is a general view of the intravenous fluid administration catheter assembly of the invention;

FIG. 2 is a general view, at a larger scale, of the multi-inlet connector of the assembly of FIG. 1 and FIG. 3 is a general view of "the sole administration" components of the assembly of FIG. 1, downstream of all containers of main and additional liquids.

Referring to FIG. 1, the intravenous (IV) fluid administration catheter assembly comprises a standard stand 1, here with a vertical column 2, a four arm mounting base 3 with four wheels 8 for moving the stand and, on top of the column, two hooks 4, 5, onto one 5 of which a bottle 6 is hung up, the assembly being represented in use. Bottle 6 is a container filled up with a main liquid 9, usually serum to be delivered into a patient blood stream, here into one 7 of his hands. The line from the bottle 6 to the hand 7 is an IV line 10. The IV line, the end of which is called the catheter, is inserted into a vein by means of a needle which is removed after the insertion. Between the bottle 6 and the hand 7, there is a multi-inlet connector 11 and other components, not represented in FIG. 1. The connector 11 is connected to the bottle 6 by a spike inlet tubing 12 and, to the hand 7, by an outlet tubing 13.

Referring now to FIG. 3, the upstream end of tubing 12 of the assembly comprises a spike 14 to be introduced into bottle 6 and which, not in use, can be covered by a cap 15. Spike 14 is connected here to a vented chamber 16 including a filter. Chamber 16, downstream of it, is connected to a roller clamp 17, to generate a flow of drops, connected, still downstream, to a flow regulator 18, to adjust the flow of drops to be administered to the patient. The flow regulator 18 is connected to the connector 11. All the above introduced components are provided on tubing 12.

Tubing 13 includes here, but this is optional, a one-inlet needleless connector 19 in case a further drug had to be administered to the patient. The end of tubing 13, opposite connector 11, includes, as is well known in the art, a male luer lock 20, to be secured, but not shown, to a female luer lock of a luer syringe 30 (FIG. 1) to be introduced into the body of the patient. When the assembly is not in use, the male luer lock 20 is covered by a cap 21.

The multi-inlet connector 11 comprises here four inlets 111-114 (FIG. 2). Tubing 12 is connected to inlet 111. Three other small tubings 22, 23, 24 are connected to inlets 112, 113, 114, respectively.

The ends of tubings 22-24 are provided, each, with a (small) needleless connector (25-27) including a non-return valve (35-37) for preventing air from getting into the connector. The valves of these connectors move to an open state when other connectors, along with partial mini assemblies of a similar nature as the one described above, with a container 40 and tubing 41, are secured thereto, for administering additional medical fluids through catheter tubing 13.

The length of the various tubings is an important feature of the assembly described above.

The length of tubing 12, from spike 14 to connector 11, which is the spike inlet tubing of the connector, is determined for, during use of the assembly with bottle 6 filled up with a main liquid 9, keeping the multi-inlet connector 11 hung up on hook 5 of stand 1 thanks to the weight of the components and the tubing. Thanks to that feature, all the tubings connected to the multi-inlet connector 11, upstream of it, do not interfere with the outlet tubing 13. The space around it, up to the patient, is free, there is no tubing traffic close to the patient.

Just to give ideas and strictly by way of example, the length of tubing 12, between chamber 16 and regulator 18 could be about 20 cm, between regulator 18 and connector 11, about 10 cm. Thus, the spike inlet tubing 12, here, has a length of about 30 cm. The height of column 2 of stand 1 being about the height of a human being, it is clear that connector 11 hangs up on hook 5. The length of tubings 22-24 could be about 5 cm and, of tubing 13, about 150 up 200 cm.

According to the above example, the outlet tubing 13, which has a length of about 150 to 200 cm, compared with the inlet tubing 12, with a length of 30 cm, is about 5 to 7, 6 times longer. However, it should be pointed out that an outlet tubing only about three times longer than the inlet tubing would already avoid the tubing traffic.

The invention claimed is:

1. An intravenous fluid administration catheter assembly comprising:
    a stand (1) with a hook (5) for hanging a container (6) of a main liquid,
    a spike (14) to be introduced into the container of main liquid (6),
    a multi-inlet connector (11) having a through channel therein, the through channel having a first end and a second end,
    a spike inlet tubing (12) to be connected directly to the container of main liquid (6) through the spike (14) the spike inlet tubing being connected to the first end of the through channel of the multi-inlet connector,
    inlet tubings (22-24) to be connected to containers (40) of additional liquids, wherein the free end of the additional liquid inlet tubings (22-24) is closed by a non-return valve (35-37) provided within a needleless connector (25-27), the valve being arranged normally in a closed state and to open when a container is connected to the inlet, and
    an outlet tubing (13) to be connected to a luer syringe (30) to be introduced into a patient (7), the outlet tubing connected to the second end of the through channel of the multi-inlet connector, thereby allowing the main liquid to flow from the container to the luer syringe via the through channel;
    wherein the assembly is a closed system from the spike to the patient, no air can come into the assembly, the assembly being further devoid of a cock to be actuated,
    wherein the length of the spike inlet tubing (12), extending between the spike (14) and the connector (11), is determined for, during use of the assembly with the container of main liquid (6), keeping the connector (11) hung up on the hook (5) of the stand (1) through the spike (14) and the container of main liquid (6), due to gravity.
2. The assembly according to claim 1, wherein the spike inlet tubing (12) has a length of about 30 cm.

* * * * *